United States Patent [19]

Yamamoto et al.

[11] Patent Number: 5,138,109
[45] Date of Patent: Aug. 11, 1992

[54] PROCESS FOR PREPARING HALOGENATED ALKYL

[75] Inventors: Michio Yamamoto; Masaru Ishino; Motoo Hazama, all of Osaka; Shigefumi Tokumasu, Oita, all of Japan

[73] Assignee: Sumitomo Chemical Company, Ltd., Osaka, Japan

[21] Appl. No.: 785,247

[22] Filed: Nov. 4, 1991

Related U.S. Application Data

[63] Continuation of Ser. No. 467,482, Jan. 19, 1990, abandoned.

[30] Foreign Application Priority Data

Jan. 23, 1989 [JP] Japan .................................. 1-14634

[51] Int. Cl.$^5$ .............................................. C07C 17/28
[52] U.S. Cl. ..................................................... 570/257
[58] Field of Search ........................................ 570/257

[56] References Cited

U.S. PATENT DOCUMENTS 2,419,500 11/1947 Peterson et al. ................. 570/257
2,501,597 3/1950 Detling ............................. 570/257
2,533,052 12/1950 Schmerling .
3,365,506 1/1968 Burk, Jr. et al. .

FOREIGN PATENT DOCUMENTS 124415 2/1977 Fed. Rep. of Germany .

OTHER PUBLICATIONS

Soviet Inventions Illustrated, Section CH, week B36, Oct. 17, 1979, p. 10.

*Primary Examiner*—Howard T. Mars
*Attorney, Agent, or Firm*—Birch, Stewart, Kolasch & Birch

[57] ABSTRACT

A halogenated alkyl of the formula:

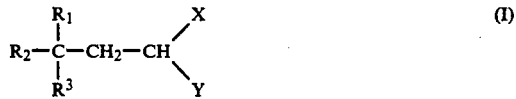

wherein $R_1$, $R_2$ and $R_3$ are the same or different and each is a lower alkyl group, X is chlorine atom or a bromine atom and Y is a hydrogen atom or a halogen atom is prepared in high conversion and high selectivity by reacting a tertiary halogenated alkyl of the formula:

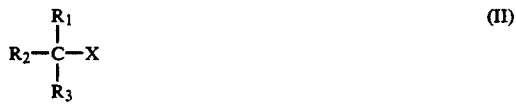

wherein $R_1$, $R_2$, $R_3$ and X are the same as defined above with an ethylene derivative of the formula:

$$CH_2=CH-Y \quad (III)$$

wherein Y is the same as defined above in the presence of a liquid catalyst comprising aluminum chloride and an alkylbenzene of the formula:

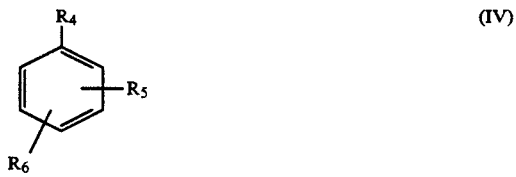

wherein $R_4$, $R_5$ and $R_6$ are the same or different and each is a lower alkyl group or a hydrogen atom provided that at least one of them is a lower alkyl group.

21 Claims, No Drawings

PROCESS FOR PREPARING HALOGENATED ALKYL

This application is a continuation of application Ser. No. 07/467,482 filed on Jan. 19, 1990, now abandoned.

BACKGROUND OF THE INVENTION

1. Field of the Invention

The present invention relates to a novel process for preparing a halogenated alkyl. More particularly, the present invention relates to a process for preparing a halogenated alkyl comprising reacting a tertiary halogenated alkyl with an ethylene derivative in the presence of a liquid catalyst comprising aluminum chloride and an alkylbenzene.

2. Description of the Related Art

A halogenated alkyl can be prepared through an addition reaction of a tertiary halogenated alkyl and an ethylene derivative in the presence of a catalyst comprising aluminum chloride, and this reaction is known as a Friedel-Crafts related reaction (see, for example, G.A. Olah, "Friedel Crafts and Related Reactions", Vol. II, 1133 (1964), Interscience Publishers (N.Y.)).

The handling of aluminum chloride in an industrial scale is very difficult, since aluminum chloride solidifies and clogs a supply inlet or a supply line of a reaction system because it is a hygroscopic solid, or it tends to generate a corrosive gas which prevents smooth operation of a production apparatus and sometimes significantly deteriorates catalytic activity. It is difficult to handle aluminum chloride safely, since it generates a stimulative gas.

Further, aluminum chloride has a high catalytic activity only in a temperature range between $-40°$ C. and $-10°$ C. Therefore, it requires a cooling equipment and large energy costs. In addition, the use aluminum chloride provides a final product in an unsatisfactory yield of 50 to 75% at the highest.

SUMMARY OF THE INVENTION

One object of the present invention is to provide a catalyst for a reaction of a tertiary halogenated alkyl and an ethylene derivative to prepare a halogenated alkyl, which catalyst has a high catalytic activity at a comparatively high temperature and is safely and stably supplied.

Another object of the present invention is to provide a novel process for preparing a halogenated alkyl in a high yield.

These and other objects are accomplished by a process for preparing a halogenated alkyl of the formula:

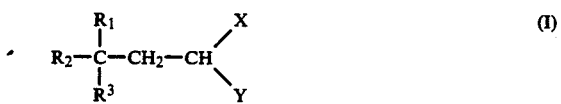 (I)

wherein $R_1$, $R_2$ and $R_3$ are the same and different and each is a lower alkyl group, X is a chlorine atom or a bromine atom and Y is a hydrogen atom or a halogen atom, which process comprises reacting a tertiary halogenated alkyl of the formula:

 (II)

wherein $R_1$, $R_2$, $R_3$ and X are the same as defined above with an ethylene derivative of the formula:

$$CH_2=CH-Y \quad (III)$$

wherein Y is the same as defined above in the presence of a liquid catalyst comprising aluminum chloride and an alkylbenzene of the formula:

 (IV)

wherein $R_4$, $R_5$ and $R_6$ are the same and different and each is a lower alkyl group or a hydrogen atom provided that at least one of them is a lower alkyl group.

DETAILED DESCRIPTION OF THE INVENTION

In the general formulas, the lower alkyl group for $R_1$, $R_2$ and $R_3$ is preferably an alkyl group having 1 to 4 carbon atoms such as a methyl group, an ethyl group, a propyl group, or a butyl group. The substituent Y includes the hydrogen atom and the halogen atoms such as a fluorine atom, a chlorine atom, a bromine atom and a iodine atom.

According to the present invention, the halogenated alkyl (I) is effectively prepared. Examples of the halogenated alkyl (I) are 1-chloro-3,3-dimethylbutane, 1-bromo-3,3-dimethylbutane, 1,1-dichloro-3,3-dimethylbutane, 1,1-dibromo-3,3-dimethylbutane, 1-bromo-1-chloro-3,3-dimethylbutane, 1-chloro-3,3-dimethylpentane, 1-bromo-3,3-dimethylpentane, 1,1-dibromo-3,3-dimethylpentane, 1,1-dichloro-3,3-dimethylpentane, 1-chloro-3,3,4-trimethylpentane, 1-bromo-3,3,4-trimethylpentane and the like.

As the halogen atom for X of the tertiary halogenated alkyl (II), a chlorine atom or a bromine atom is preferred.

Specific examples of the tertiary halogenated alkyl (II) are tert.-butyl chloride, tert.-butyl bromide, 2-chloro-2-methylbutane, 2-bromo-2-methylbutane, 2-chloro-2-methylpentane, 2-bromo-2-methylpentane, 2-chloro-2-methyl-hexane, 2-bromo 2-methylhexane, 2-chloro-2,3-dimethylbutane, 2-bromo-2,3-dimethylbutane and the like.

Specific examples of the ethylene derivative (III) are ethylene, vinyl fluoride, vinyl chloride, vinyl bromide and vinyl iodide.

The lower alkyl group for $R_4$, $R_5$ and $R_6$ of the alkyl benzene (IV) is preferably an alkyl group having 1 to 4 carbon atoms such as methyl, ethyl, propyl or butyl. Specific examples of the alkylbenzene are toluene, xylene, mesitylene, ethylbenzene, cymene (e.g. m-cymene), cumene, tert.-butyltoluene, di-tert.-butyltoluene, diethylbenzene, diisopropylbenzene, methyldiisopropylbenzene (e.g. 1-methyl-3,5-diisopropylbenzene) and the like. Among them, ethylbenzene, m-cymene and 1-methyl-3,5-diisopropylbenzene are preferred. The isomers of the alkylbenzene which has two or three substituents on the benzene ring can be used. A mixture of two or more alkylbenzenes may be used.

The catalyst to be used in the present invention is a liquid catalyst comprising a complex compound of aluminum chloride and the alkylbenzene (IV). The catalyst may contain hydrogen chloride which may be produced in the production of the catalyst.

The catalyst of the present invention can be prepared in any preparation mode. For example, metal aluminum and the alkylbenzene (IV) are reacted in a specified ratio at a temperature of 30° C. to 150° C., preferably 40° C. to 110° C. under atmospheric pressure or elevated pressure while supplying hydrogen chloride gas. Alternatively, anhydrous aluminum chloride and the alkylbenzene (IV) are reacted in a specified ratio at a temperature of −30° C. to +150° C., preferably −20° C. to +110° C. under atmospheric pressure or elevated pressure while supplying hydrogen chloride gas.

In any case, amounts of the alkylbenzene (IV) and the hydrogen chloride gas are not critical. Preferably, the alkylbenzene (IV) is used in an amount of 0.3 to 10 moles, and the hydrogen chloride gas is used in an amount of 0.4 to 20 moles, per one mole of metal aluminum or anhydrous aluminum chloride. When the alkylbenzene (IV) is used in an excess amount, the formed complex compound and the alkylbenzene separate in two phases, and the complex compound can be easily recovered by any of conventional methods such as separation.

A concentration of aluminum chloride in the liquid catalyst is from 20 to 60 % by weight, preferably from 30 to 55% by weight.

A molar ratio of the tertiary halogenated alkyl (II) to the ethylene derivative (III) is not critical. Usually, said molar ratio is from 1:0.2 to 1:5, preferably from 1:0.5 to 1:3.

The amount of the catalyst to be used in the present process is from 0.001 to 0.3 mole, preferably from 0.005 to 0.1 mole in terms of aluminum chloride per one mole of the tertiary halogenated alkyl (II).

The reaction temperature in the present process is usually from −30° C. to +50° C. When the reaction temperature is lower than −30° C., the reaction rate becomes too low, while when the reaction temperature is higher than 50° C., the catalyst tends to be deactivated and/or side reactions tend to proceed. Preferably, the reaction temperature is from −15° C. to +20° C.

The reaction pressure is usually from 0 to 100 kg/cm$^2$, preferably from 0 to 10 kg/cm$^2$ in view of handle-ability and apparatus design.

Although the reaction according to the present invention may be carried out in the absence of a solvent, a solvent which is inactive to the reaction can be used. Examples of the solvent are methylene dichloride, 1,2-dichloroethane, chloroform, carbon tetrachloride, n-tridecane, n-pentane, o-dichlorobenzene and the like.

The produced halogenated alkyl (I) can be recovered from the reaction mixture by any of conventional methods such as distillation after removing the catalyst from the reaction mass by any of the conventional methods.

PREFERRED EMBODIMENTS OF THE INVENTION

Practically and presently preferred embodiments of the present invention will be illustrated by following examples.

Reference Examples 1, 2, 6–9, 12, 13 & 17

Preparation method (a) of the catalyst

In a pressure reaction vessel, the alkylbenzene shown in Table 1 and metal aluminum were charged in amounts shown in Table 1. Through the mixture, hydrogen chloride gas was bubbled at a temperature of Table 1 under pressure of Table 1.

During the reaction, generated hydrogen gas was removed continuously when the pressure was atmospheric pressure, or at certain intervals when the pressure is elevated pressure. When the excess amount of the alkylbenzene was used, a brown liquid complex compound (catalyst) comprising aluminum chloride and the alkylbenzene was recovered by separation.

The results are shown in Table 1.

Reference Examples 3–5, 10, 11 & 14–16

Preparation method (b) of the catalyst

In a pressure reaction vessel, the alkylbenzene shown in Table 1 and anhydrous aluminum chloride were charged in amounts shown in Table 1. Through the mixture, hydrogen chloride gas was bubbled at a temperature of Table 1 under pressure of Table 1.

When the excess amount of the alkylbenzene was used, a brown liquid complex compound (catalyst) comprising aluminum chloride and the alkylbenzene was recovered by separation.

The results are shown in Table 1.

EXAMPLES 1–7

In a 300 ml four-necked round glass flask equipped with a thermometer, a magnetic stirrer covered with polytetrafluoroethylene was placed, and the tertiary halogenated alkyl shown in Table 2 (0.5 mole) was charged and kept at 0° C.

Then, the liquid catalyst prepared in each of Reference Examples and the ethylene derivative shown in Table 2 (0.55 mole) were continuously charged over about 2 hours through different inlets under atmospheric pressure.

Since the reaction was exothermic, the internal temperature was adjusted at 0° C. with a cooling bath. After the supply of the liquid catalyst and the ethylene derivative, the internal temperature was kept at 0° C. for one hour to complete the reaction.

The conversion and the selectivity in Table 2 were calculated according to the following equations:

$$\text{Conversion (\%)} = \frac{A - B}{A} \times 100$$

$$\text{Selectivity (\%)} = \frac{C}{A - B} \times 100$$

wherein A is an amount (mole) of the charged tertiary halogenated alkyl, B is an amount (mole) of the recovered tertiary halogenated alkyl, and C is an amount (mole) of the produced halogenated alkyl.

EXAMPLE 8

In the same manner as in Example 2 but keeping the internal temperature at about 8° C. and using 2.30% by mole of the liquid catalyst prepared in Reference Example 6, the reaction was carried out. The results are shown in Table 2.

COMPARATIVE EXAMPLE 1

In the same manner as in Example 1 but using commercially available anhydrous aluminum chloride particles which had been ground in place of the liquid catalyst of the present invention and charging it in one portion, the reaction was carried out. The results are shown in Table 2.

COMPARATIVE EXAMPLE 2

In the same manner as in Example 8 but using the same anhydrous aluminum chloride as used in Comparative Example 1 in place of the catalyst of the present invention, the reaction was carried out. The results are shown in Table 2.

EXAMPLE 9

In a 300 ml glass autoclave equipped with a thermometer and a stirrer, the tertiary halogenated alkyl shown in Table 2 (0.5 mole) was charged, and the internal temperature was adjusted at 0° C.

Then, the liquid catalyst prepared in Reference Example 10 and the ethylene derivative shown in Table 2 (0.55 mole) were continuously charged over about 2 hours through different inlets under internal pressure of 0 to 2 kg/cm$^2$.

Since the reaction was exothermic, the internal temperature was kept at 0° C. with a cooling bath. After the supply of the liquid catalyst and the ethylene derivative, the internal temperature was kept at 0° C. for one hour to complete the reaction.

After the reaction completed, the reaction product was analyzed in the same manner as in Example 1.

The results are shown in Table 2.

EXAMPLES 10, 11 & 12

In the same manner as in Example 9 but keeping the reaction temperature at −10° C. in Example 10, at −5° C. in Example 11 or +15° C. in Example 12 and using the catalyst shown in Table 2, the reaction was carried out. The results are shown in Table 2.

EXAMPLE 13

In the same manner as in Example 9 but adjusting the reaction pressure at 5 kg/cm$^2$ and using the catalyst shown in Table 2, the reaction was carried out. The results are shown in Table 2.

EXAMPLE 14

In the same manner as in Example 9 but using 1,2-dichloroethane (20 g) as a solvent and the catalyst shown in Table 2, the reaction was carried out. The results are shown in Table 2.

EXAMPLES 15-19

In the same manner as in Example 1 but using the tertiary halogenated alkyl, the ethylene derivative and the catalyst all shown in Table 2, the reaction was carried out. The results are shown in Table 2.

TABLE 1

| Ref. Ex. No. | Preparation method | Alkylbenzene | (molar ratio[1]) | HCl gas molar ratio[2] | Temp. (°C.) | Pressure (kg/cm$^2$) | Concentration of aluminum chloride (wt %) |
|---|---|---|---|---|---|---|---|
| 1 | a | Toluene | (2.50) | >4 | 70 | 0 | 36 |
| 2 | a | ↑ | (1.50) | >4 | ↑ | ↑ | 46 |
| 3 | b | ↑ | (4.00) | 1.5 | 20–40 | 0–1 | 26 |
| 4 | b | ↑ | (2.18) | 1.5 | ↑ | ↑ | 36 |
| 5 | b | ↑ | (1.37) | 1.5 | 5–20 | ↑ | 45 |
| 6 | a | Ethylbenzene | (2.20) | >4 | 70 | 0 | 36 |
| 7 | a | ↑ | (1.20) | 4 | 80–100 | 0–4 | 45 |
| 8 | a | m-Xylene | (2.20) | >4 | 70 | 0 | 36 |
| 9 | a | p-Cymene | (1.73) | >4 | 70 | 0 | 36 |
| 10 | b | ↑ | (0.89) | 1.2 | 20–40 | 0–1 | 46 |
| 11 | b | m-Cymene | (1.22) | 1.2 | 10–30 | ↑ | 40 |
| 12 | a | 1-Methyl-3,5-diisopropylbenzene | (1.14) | 4.5 | 60–80 | 0–4 | 36 |
| 13 | a | ↑ | (0.41) | 5.0 | ↑ | 0 | 55 |
| 14 | b | ↑ | (3.00) | 0.8 | 20–40 | ↑ | 36 |
| 15 | b | ↑ | (0.75) | 0.5 | 70–80 | 0–1 | 47 |
| 16 | b | ↑ | (0.60) | 0.5 | 20–40 | 0 | 51 |
| 17 | a | Mesitylene | (1.26) | 4.1 | 70–90 | 0 | 41 |

Note:
[1] A molar ratio of the alkylbenzene to metal aluminum or aluminum chloride.
[2] A molar ratio of HCl gas to metal aluminum or aluminum chloride.

TABLE 2

| Ex. No. | Tertiary halogenated alkyl | Ethylene derivative | Catalyst Ref. Ex. No. | Mol %[1] | Product | Conversion (%) | Selectivity (%) |
|---|---|---|---|---|---|---|---|
| 1 | tert.-Butyl chloride | Ethylene | 1 | 1.63 | 1-Choro-3,3-dimethylbutane | 99.1 | 83.0 |
| 2 | ↑ | ↑ | 6 | 1.70 | ↑ | 99.1 | 90.9 |
| 3 | ↑ | ↑ | 8 | 2.78 | ↑ | 98.6 | 78.2 |
| 4 | ↑ | ↑ | 2 | 1.43 | ↑ | 99.0 | 84.4 |
| 5 | ↑ | ↑ | 9 | 1.04 | ↑ | 98.5 | 86.4 |
| 6 | tert.-Butyl bromide | ↑ | 1 | 1.00 | 1-Bromo-3,3-dimethylbutane | 97.1 | 90.1 |
| 7 | tert.-Butyl chloride | Vinyl bromide | 1 | 2.50 | 1-Bromo-1-chloro-3,3-dimethylbutane | 98.2 | 80.2 |
| 8 | ↑ | Ethylene | 6 | 2.30 | 1-Chloro-3,3-dimethylbutane | 98.2 | 81.5 |
| 9 | ↑ | ↑ | 10 | 1.92 | ↑ | 100.0 | 86.7 |
| 10 | ↑ | ↑ | 7 | 2.16 | ↑ | 100.0 | 88.3 |
| 11 | ↑ | ↑ | 11 | 2.26 | ↑ | 98.7 | 89.2 |
| 12 | ↑ | ↑ | 12 | 2.30 | ↑ | 98.9 | 85.9 |

TABLE 2-continued

| Ex. No. | Tertiary halogenated alkyl | Ethylene derivative | Catalyst Ref. Ex. No. | Mol %[1] | Product | Conversion (%) | Selectivity (%) |
|---|---|---|---|---|---|---|---|
| 13 | ↑ | ↑ | 14 | 1.98 | ↑ | 99.9 | 85.1 |
| 14 | ↑ | ↑ | 14 | 2.68 | ↑ | 94.8 | 86.5 |
| 15 | ↑ | Vinyl chloride | 7 | 2.50 | 1,1-Dichloro-3,3-dimethylbutane | 97.3 | 80.1 |
| 16 | tert.-Butyl bromide | ↑ | 7 | 2.50 | 1-Bromo-1-chloro-3,3-dimethylbutane | 98.8 | 81.2 |
| 17 | tert.-Butyl chloride | Ethylene | 17 | 2.60 | 1-Chloro-3,3-dimethylbutane | 98.2 | 77.6 |
| 18 | 2-Chloro-2-methylbutane | ↑ | 10 | 2.50 | 1-Chloro-3,3-dimethylpentane | 98.7 | 76.8 |
| 19 | 2-Bromo-2-methylbutane | Vinyl bromide | 10 | 2.50 | 1,1-Dibromo-3,3-dimethylpentane | 98.9 | 77.0 |
| C.1 | tert.-Butyl chloride | Ethylene | AlCl$_3$ | 1.63 | 1-Chloro-3,3-dimethylbutane | 84.3 | 70.1 |
| C.2 | ↑ | ↑ | ↑ | 2.30 | ↑ | 75.8 | 64.0 |

Note:
[1] A mole percentage of aluminum chloride based on the tertiary halogenated alkyl.

What is claimed is:

1. A process for preparing a halogenated alkyl of the formula:

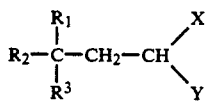

(I)

wherein $R_1$, $R_2$ and $R_3$ are the same or different and each is a lower alkyl group, X is a chlorine atom or a bromine atom and Y is a hydrogen atom or a halogen atom, which process comprises reacting a tertiary halogenated alkyl of the formula:

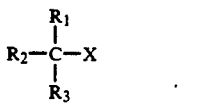

(II)

wherein $R_1$, $R_2$, $R_3$ and X are the same as defined above with an ethylene derivative of the formula:

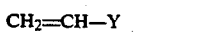

$$CH_2=CH-Y \quad (III)$$

wherein Y is the same as defined above in the presence of a liquid catalyst comprising aluminum chloride and an alkyl-benzene of the formula:

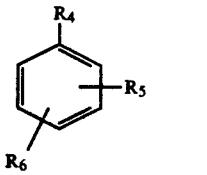

(IV)

wherein $R_4$, $R_5$ and $R_6$ are the same or different and each is a lower alkyl group or a hydrogen atom provided that at least one of $R_4$, $R_5$ and $R_6$ is a lower alkyl group.

2. The process according to claim 1, wherein the tertiary halogenated alkyl is at least one selected from the group consisting of tert.-butyl chloride, tert.-butyl bromide, 2-chloro-2-methylbutane and 2-bromo-2-methylbutane.

3. The process according to claim 1, wherein the ethylene derivative is at least one selected from the group consisting of ethylene, vinyl chloride and vinyl bromide.

4. The process according to claim 1, wherein the halogenated alkyl is at least one selected from the group consisting of 1-chloro-3,3-dimethylbutane, 1-bromo-3,3-dimethylbutane, 1-bromo-1-chloro-3,3-dimethylbutane, 1,1-dichloro-3,3-dimethylbutane, 1-chloro-3,3-dimethylpentane and 1,1-dibromo-3,3-dimethylpentane.

5. The process according to claim 1, wherein the alkylbenzene is at least one selected from the group consisting of toluene, xylene, mesitylene, ethylbenzene, cymene and methyldiisopropylbenzene.

6. The process according to claim 5, wherein the alkylbenzene is at least one selected from the group consisting of ethylbenzene, m-cymene and 1-methyl-3,5-diisopropylbenzene.

7. The process according to claim 1, wherein a molar ratio of the tertiary halogenated alkyl and the ethylene derivative is from 1:0.2 to 1:5.

8. The process according to claim 1, wherein the liquid catalyst is used in an amount of 0.001 to 0.3 moles in terms of aluminum chloride per one mole of the tertiary halogenated alkyl.

9. The process according to claim 8, wherein the liquid catalyst is used in an amount of 0.005 to 0.1 moles in terms of aluminum chloride per one mole of the tertiary alkyl.

10. The process according to claim 1, wherein a concentration of aluminum chloride in the liquid catalyst is from 20 to 60 % by weight.

11. The process according to claim 10, wherein the concentration of the aluminum chloride in the liquid catalyst is from 30 to 55 % by weight.

12. The process according to claim 1, wherein the reaction temperature is from −30° C. to +50° C.

13. The process according to claim 12, wherein the reaction temperature is from −15° C. to +20° C.

14. The process according to claim 1, wherein the tertiary halogenated alkyl is at least one selected from the group consisting of tert.-butyl chloride, tert.-butyl bromide, 2-chloro-2methylbutane and 2-bromo-2-methylbutane; wherein the ethylene derivative is at least one selected from the group consisting of ethylene, vinyl chloride and vinyl bromide; wherein the halogenated alkyl is at least one selected from the group consisting of 1-chloro-3,3-dimethylbutane, 1-bromo-3,3-dimethylbutane, 1-bromo-1-chloro-3,3-dimethylbutane, 1,1-dichloro-3,3-dimethylbutane, 1-chloro-3,3-dimethylpentane and 1,1-dibromo-3,3-dimethylpentane; and wherein the alkylbenzene is at least one selected from the group consisting of toluene, xylene, mesitylene, ethylbenzene, cymene and methyldiisopropylbenzene.

15. The process according to claim 14, wherein the alkylbenzene is at least one selected from the group consisting of ethylbenzene, m-cymene and 1-methyl-3,5-diisopropylbenzene.

16. The process according to claim 7, wherein the liquid catalyst is used in an amount of 0.001 to 0.3 moles in terms of aluminum chloride per one mole of the tertiary halogenated alkyl.

17. The process according to claim 16, wherein a concentration of aluminum chloride in the liquid catalyst is from 20 to 60% by weight.

18. The process according to claim 1, wherein a molar ratio of the tertiary halogenated alkyl and the ethylene derivative is from 1:0.5 to 1:3.

19. The process according to claim 1, wherein the reaction pressure is from 0 to 100 kg/cm$^2$.

20. The process according to claim 1, wherein the reaction pressure is from 0 to 10 kg/cm$^2$.

21. The process according to claim 1, wherein the reaction is carried out in a solvent selected from the group consisting of methylene dichloride, 1,2-dichloroethane, chloroform, carbon tetrachloride, n-tridecane, n-pentane and o-dichlorobenzene.

* * * * *